United States Patent [19]

Campbell

[11] Patent Number: 5,070,084

[45] Date of Patent: Dec. 3, 1991

[54] TREATMENT OF SYMPATHETICALLY MAINTAINED PAIN

[76] Inventor: James N. Campbell, 600 N. Wolfe St., Baltimore, Md. 21205

[21] Appl. No.: 485,156

[22] Filed: Feb. 26, 1990

[51] Int. Cl.⁵ .......................................... A61K 31/495
[52] U.S. Cl. .................................................. 514/248
[58] Field of Search ........................................ 514/248

[56] References Cited

U.S. PATENT DOCUMENTS

| 4,201,211 | 5/1980 | Chandrasekaran et al. | 514/248 |
| 4,250,191 | 2/1981 | Edwards | 514/248 |
| 4,310,535 | 1/1982 | Pierpaoli | 514/248 |
| 4,443,441 | 4/1984 | Galin | 514/248 |
| 4,801,587 | 1/1989 | Voss et al. | 514/248 |

OTHER PUBLICATIONS

Janig, W., *Trends in NeuroSciences* 8(11), 471–77 (1985).
Lohand et al., *J. Neurol. Neurosurg. Psychiat.* 41(7), 664–71 (1978).
Naftchi, N., *Chem. Abst.* 110(9):69410r.
Nakagawa et al., *Chem. Abst.* 111(2):12526z.
Nakagawa et al., *Chem. Abst.* 110(12):101838z.
Gonzales et al., *J. Neurochem.* 53(5), 1959–98 (1989).
Hobelmann et al., *Microsurg.* 10(2), 151–53 (1989).
Price et al., *Pain* 36(3), 273–88 (1989).

*Primary Examiner*—Stanley J. Friedman
*Attorney, Agent, or Firm*—Kilpatrick & Cody

[57] ABSTRACT

Method of diagnosing and treatment of sympathetically maintained pain. Sympathetically maintained pain is diagnosed and treated using the method of injecting or transdermally applying an α-adrenergic blocking agent selected from the group consisting of α-adrenergic antagonist, α-1-adrenergic antagonist, α2 adrenergic agonist, or other drug that depletes sympathetic norepinephrine. Sympathetic efferent fibers release norepinephrine which in turn activates α-adrenergic receptors. Activation of these receptors, either directly or indirectly, excites nociceptors. Activity in the nociceptors then evokes pain, and causes further discharge of nociceptors. Intravenous administration of phentolamine blocks the activation of α-adrenergic receptors which causes the pain to be relieved. The use of a clonidine, another α-adrenergic blocking agent, in a patch similarly achieved substantive pain reduction.

3 Claims, No Drawings

TREATMENT OF SYMPATHETICALLY MAINTAINED PAIN

BACKGROUND OF THE INVENTION

1. Field of the Invention

The invention relates to the diagnosis and treatment of pain.

2. Description of the Related Art

Certain patients are distinguished by having pain whose presence is dependent on sympathetic innervation of the painful area. The pain may result from skeletal, soft tissue, or nerve injury. Terms such as reflex sympathetic dystrophy, Sudek's atrophy, and causalgia have all been used to refer to such patients. However, because the link between pain and sympathetic function is often vague or not specified in much of the literature concerning these nosological designations, the term "sympathetically maintained pain" (SMP) is used to refer to that aspect of pain which is dependent on sympathetic efferent activity in the painful portion of the body.

One method of diagnosis of SMP is by assessment of the results of a local anesthetic blockade of the sympathetic ganglia (LABSG) that innervate the painful part. Intravenous regional blockage (IVRB) of sympathetic function with guanethidine has also been advocated as a means to diagnose SMP. Sympathetic blocks may not only provide a basis for diagnosis of SMP, but, may in addition, prove to be therapeutic. That is, the pain may be diminished after one or a series of block may.

Several disadvantages apply to the use of LABSG and IVRB. (1) LABSG is subject to false negative results if the local anesthetic fails to anesthetize adequately the sympathetic ganglia. (2) LABSG is subject to false positive results on two accounts: the anesthetic may reach the somatic afferents in the nearby nerve roots and produce pain relief because of concurrent somatic blockade, and certain afferents may in addition course with sympathetic efferents. (3) Certain patients tolerate poorly the application of the tourniquet required with IVRB. (4) LABSG involves strategic localization of the needle prior to injection, so fluoroscopy is often needed. (5) With IVRB the guanethidine may enter the systemic circulation and produce unfavorable side effects. (6) A series of complications have been reported with LABSG, which include pneumothorax, injury to the kidney, inadvertent systemic application, spinal anesthesia, hemorrhage, etc. (7) It is difficult to evaluate placebo responses with both LABSG and IVRB.

A method of diagnosis and treatment that eliminates the recited difficulties of current procedures used for patients with SMP is not found in the prior art.

Therapeutic uses of the α-adrenergic compounds, for example, phentolamine and clonidine, are known in the art.

U.S. Pat. No. 4,801,157, issued Jan. 1, 1989, discloses the use of phentolamine as a vasodilator to treat impotence.

U.S. Pat. No. 4,310,535, issued Jan. 12, 1982, discloses the systemic use of phentolamine in combination with other drugs for use in the control of immune reactions.

The systemic administration of phentolamine and clonidine for controlling hypertension is disclosed in U.S. Pat. No. 4,250,191.

α-Adrenergic drugs have been found to be useful in the stabilization of intraocular lenses, as disclosed in U.S. Pat. No. 4,443,441.

U.S. Pat. No. 4,201,211, issued May 6, 1980, discloses the use of a clonidine patch for therapeutic use as a stimulant for the central nervous system.

Other uses have also been reported for α-adrenergic antagonists and agonists. However, the prior art does not disclose the painful site use of α-adrenergic compounds such as phentolamine and clonidine for the diagnosis and treatment of sympathetically maintained pain.

SUMMARY OF THE INVENTION

It is an object of the invention to provide a method of diagnosis for sympathetically maintained pain that has a low incidence of false positive and false negatives.

It is another object of the invention to provide a method of diagnosis and treatment of sympathetically maintained pain that has a low incidence of adverse reactions and relatively minor complications.

Finally, it is an object of the invention to provide a method of treatment for sympathetically maintained pain that results in pain remission lasting for substantial periods of time, in some cases, even permanently.

The invention is a method of diagnosing and treating sympathetically maintained pain comprising the single step of introducing a drug selected from the group comprising an α-adrenergic antagonist, α-1-adrenergic antagonist, α2 adrenergic agonist, or a drug that depletes norepinephrine from the sympathetic terminals, a process referred to herein as sympatholysis with said drug administered in an amount effective to cause measurable pain relief.

DETAILED DESCRIPTION OF THE INVENTION

The inventor has discovered the mechanism that causes sympathetically maintained pain. Sympathetic efferent fibers release norepinephrine which in turn activates α-adrenergic receptors. Activation of these receptors, either directly or indirectly, excites nociceptors. Activity in the nociceptors then evokes pain, and in addition, elicits further activity in the sympathetic efferent fibers. This, in turn, results in further discharge of the nociceptors.

Evidence for this mechanism includes the follows: (1) The IVRB with guanethidine works through a peripheral mechanism presumably via depletion of sympathetic terminals of norepinephrine. (2) LABSG probably works by preventing peripheral release of norepinephrine. (3) Oral administration of the α-adrenergic antagonist, phenoxybenzamine, decreases pain in SMP disorders. (4) Pain is reestablished by local injection of epinephrine into the ordinarily painful area in SMP patients under the influence of a LABSG. (5) Local administration of epinephrine to experimentally produce neuromas in rats evokes neural activity, as does electrical stimulation of the sympathetic chain. This effect is blocked by systemic administration of the α-adrenergic antagonist, phentolamine.

The Examples below are specific embodiments of the invention and are in no way intended to limit the scope of the invention disclosed herein.

EXAMPLE 1

Intravenous Administration of Phentolamine to Diagnose SMP

If peripheral α-adrenergic receptors are blocked completely, skin temperature would approach core temperature. Such a blockage would produce profound hypotension and a reflex tachycardia. Therefore, a cumulative dose of phentolamine was selected such that the heart rate did not exceed 150 beats per minute and the effects on blood pressure were mild. This dose ranged from 35 mg to 45 mg over a 30 minute period. Preliminary studies suggested that this amount of phentolamine effectively relieved pain in patients with SMP.

The heart rate, systolic and diastolic blood pressure changes produced by phentolamine in a typical patient were relatively mild. In the first seven patients phentolamine alone was given. In these patients the heart rate increased moderately. In subsequent sessions, patients pretreated with propranolol 1-2 mg showed minimal increase in pulse rate. Blood pressure was little effected regardless of whether propranolol was given as patients were maintained in a supine position.

One patient, an 18 year old woman, was treated for severe pain in the right foot. The patient has a thorough examination but no clear initiating cause of the pain was determined. The patient was disabled and could not walk due to the severity of the pain. A thorough neurological exam disclosed a restricted zone of hyperalgesia on the plantar surface of the foot that was consistent over several examinations. No psychiatric problems were present in an otherwise normal productive college student performing well in school.

The patient was diagnosed SMP and then underwent local LABSG, and the administration of IV phentolamine systemically.

Placebo trials indicated that patients showed no change in pain when normal saline was injected IV.

Phentolamine given IV with an accumulated doses of 25 mg over 15 minutes led to an 80% reduction pain as measured by visual analysis scores and LABSG led to 50% relief of pain in a separate study.

Ratings of stimulus-independent pain did not change for 10 minutes following the initial phentolamine administration. The first 4 boli of phentolamine (total dose=15 mg) resulted in a gradual decrease in pain of about 50%. Finally, after two further injections each of 10 mg., over 80% of the patient's pain was relieved. The slow time course of pain relief suggests that the total cumulative does is the relevant dose parameter.

Five minutes after the last phentolamine dose, 0.5 mg propranolol was given intravenously to counteract the tachycardia that was starting to become uncomfortable to the patient. This did not add appreciably to the analgesia already achieved with the α-adrenergic blockade. Propranolol was shown not to affect pain in patients. The patient's pain remained at this low level for about two hours, despite a plasma half-life of approximately 20 minutes for phentolamine. Pain gradually returned over the course of about three hours.

The LABSG procedure failed to afford long-term relief and the patient subsequently underwent a surgical lumbar sympathectomy. The patient had complete pain relief from this procedure and continues to be pain free as of 15 months post operatively.

Seventeen patients received both phentolamine and LABSG. The time of maximum relief of stimulus evoked pain correlated highly with the time at which there was maximum relief of stimulus-independent pain. All pain scores were converted to percent pain relief. The peak relief of stimulus independent pain for the LABSG compares favorably to the peak relief obtained from the phentolamine block. The range of peak relief for both procedures extended from near zero to 100%. Patients with less than 50% pain relief from both procedures were considered to have pain independent of SMP. There was a high correlation of the results of the two procedures ($r=0.78$). This shows that patients who experience substantive pain relief from LABSG also obtain substantive pain relief from phentolamine.

In five patients in whom the phentolamine block afforded more than 50% pain relief, the duration of pain relief lasted for several hours. The pain returned to within 75% of baseline with 2 to 7 hours.

Only one patient reported 45% maximum relief of pain with the LABSG but no relief with the phentolamine block.

There was a suggestion of greater specificity of results with phentolamine compared to LABSG. Of those patients who had 50% or greater pain relief following LABSG, the mean pain relief with phentolamine was 75% vs. 60% for the LABSG.

Side effects associated with the phentolamine administration other than the hemodynamic changes discussed above were minimal. The principal side effects observed were nasal stuffiness (12 patients), headache (3 patients), and dizziness (2 patients). The complications of the LABSG included mild headache, mild dizziness, back and neck pain from the needles, temporary paresis, and concurrent somatic block (thus, negating LABSG) and requiring another procedure. When patients were asked which of the two sympathetic blocks they preferred, the patients chose the phentolamine block.

EXAMPLE 2

Topical Administration of Clonidine to Treat SMP

A patient with a sciatic nerve injury was diagnosed as having SMP, based on lumbar sympathetic blockage. The patient had ongoing pain and intense hyperalgesia to both mechanical and cold stimuli in her painful zone. Clonidine was applied to the hyperalgesic zone transdermally via a 7.0 or 10.5 $cm^2$ patch (Catapres-TTS;Boehringer). These patches deliver 0.2 mg or 0.3 mg of clonidine/day for 7 days. A series of 6 patches were applied consecutively to different sites; each in place for 2-10 days. Prior to, during, and post drug application, the heat rate and blood pressure were taken and sensory testing performed. Pain evoked by mechanical and cold stimuli was rated on a scale from 0-10.

Complete relief of hyperalgesia in the skin underlying the patch was achieved from each clonidine patch. There were no adverse side effects or changes in cardiovascular parameters. The skin surrounding the patch remained hyperalgesic even in the region adjacent to the edge of the patch. At each patch site, the pain evoked by deep pressure, light brushing and cooling stimuli was reduced within 24-36 hours and was completely abolished within 48 hours following patch application. This effect persisted for more than 24 hours after removal of the patch. A local anesthetic effect is unlikely since the patch did not alter 1) the detection threshold to mechanical stimuli in the patient, or 2) the detection of the pain threshold to mechanical stimuli in a normal subject.

The local effects of clonidine suggested that peripheral adrenergic receptors play an integral role in sympathetic pain disorders. Further, it suggests that the $\alpha 2$-agonist clonidine eliminates hyperalgesia by inhibiting norepinephrine release which decreases activation of the $\alpha 1$-adrenergic receptor.

Based on the above examples and the results obtained, it is clear that any $\alpha$-adrenergic antagonist, $\alpha$-1-adrenergic antagonist, $\alpha 2$ adrenergic agonist, or other drug that depletes sympathetic norepinephrine, for example, bretylium, reserpine, phenoxybenzamine, or guanethidine will similarly relieve SMP using the method according to the invention. Further, due to the non-invasive nature of the procedure, a transdermal application of above mentioned drug according to the invention is preferred.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

I claim:

1. A method of treatment of sympathetically maintained pain comprising administering to a patient at a painful site an effective amount of an $\alpha$-adrenergic antagonist to cause measurable pain relief.

2. The method in claim 1 wherein the drug is phentolamine.

3. The method of claim 1 wherein the $\alpha$-adrenergic antagonist is administered in a pharmaceutically acceptable carrier for topical application.

* * * * *